(12) United States Patent
Russo et al.

(10) Patent No.: US 8,097,040 B2
(45) Date of Patent: Jan. 17, 2012

(54) OSTEOSYNTHESIS MODULAR PROSTHESIS, PARTICULARLY FOR HUMERUS OSTEOSYNTHESIS

(75) Inventors: Enrico Russo, Rome (IT); Raffaele Russo, Villaricca (IT)

(73) Assignee: Arthrex, Inc., Naples, FL (US)

( * ) Notice: Subject to any disclaimer, the term of this patent is extended or adjusted under 35 U.S.C. 154(b) by 643 days.

(21) Appl. No.: 11/920,753

(22) PCT Filed: May 26, 2006

(86) PCT No.: PCT/IT2006/000396
§ 371 (c)(1),
(2), (4) Date: Nov. 26, 2007

(87) PCT Pub. No.: WO2006/126238
PCT Pub. Date: Nov. 30, 2006

(65) Prior Publication Data
US 2009/0105838 A1  Apr. 23, 2009

(30) Foreign Application Priority Data
May 27, 2005  (IT) .............................. RM2005A0265

(51) Int. Cl.
*A61F 2/36* (2006.01)
(52) U.S. Cl. ................ 623/23.12; 623/23.11; 623/23.14
(58) Field of Classification Search ............... 623/17.13, 623/19.11–19.14
See application file for complete search history.

(56) References Cited

U.S. PATENT DOCUMENTS

| 4,064,567 A | 12/1977 | Burstein et al. |
| 5,609,635 A | 3/1997 | Michelson |
| 5,725,593 A * | 3/1998 | Caracciolo ................ 623/22.23 |
| 5,776,194 A * | 7/1998 | Mikol et al. ............... 623/22.42 |
| 6,302,914 B1 * | 10/2001 | Michelson ................ 623/17.16 |
| 6,783,549 B1 | 8/2004 | Stone et al. |
| 7,556,652 B2 * | 7/2009 | Angibaud et al. ......... 623/19.14 |
| 2004/0230311 A1 * | 11/2004 | Cyprien et al. ............ 623/19.11 |

FOREIGN PATENT DOCUMENTS

| EP | 0 940 126 | 9/1999 |
| FR | 2 579 454 | 10/1986 |
| FR | 2 669 528 | 5/1992 |
| FR | 2 727 005 | 5/1996 |
| WO | WO 97/15246 | 5/1997 |

* cited by examiner

*Primary Examiner* — David Isabella
*Assistant Examiner* — Joshua Levine
(74) *Attorney, Agent, or Firm* — Dickstein Shapiro LLP

(57) ABSTRACT

The present invention relates to an improved osteosynthesis modular prosthesis, particularly for humerus osteosynthesis, characterize in that it comprises a cup element (7) having a convex surface suitable to be introduced within a bone cavity, particularly within the humerus glenoid cavity, and having a concave surface suitable to contain and keep joined all the bone fragments, particularly fragments of humerus epiphysial pa (2, 3, 4), permitting vascularization and the consequent recovery of bone tissue, a stem element suitable to be introduced within a diaphyseal channel, particularly within humerus diaphyseal channel, a coupling element (9), and coupling means (10, 11) suitable to fix ends of said coupling element (9) respectively at said cup element (7) and at said stem element (8).

40 Claims, 3 Drawing Sheets

OSTEOSYNTHESIS MODULAR PROSTHESIS, PARTICULARLY FOR HUMERUS OSTEOSYNTHESIS

The present invention relates to an improved osteosynthesis modular prosthesis, particularly for humerus osteosynthesis.

More specifically, the invention concerns a modular prosthesis that can be applied for humerus osteosynthesis, permitting recover of damaged bone tissue and its vascularization.

The specification will be in the following Mainly addressed to the humerus osteosynthesis, but it is well evident that the same must not be considered limited to this specific use.

As it is well known, a large number of humerus prosthesis exists. It has been noted that shoulder pathologies and traumas are characterised by remarkable surgical complications and variants.

In fact, humerus is a longitudinal bone forming arm skeleton, and is articulated with scapula, radio and ulna. It has a substantially cylindrical shape in the diaphyseal portion, while in its upper part provides a head, inserting within the glenoid cavity. A "narrowing", known as anatomical neck is present at the base of the head.

Finally, close to the anatomical neck two relieves are present, known as large and small tuberosity.

Obviously, first aim of every shoulder surgical intervention is alleviating pain and giving mobility to the articulation.

Prostheses permitting replacing humerus head are usually endo-prosthesis, at least practically penetrating within the humerus diaphyseal channel. Further, they completely replace the humerus epiphysial portion, even in fractures where at least part of the bone tissue could be recovered or re-used, particularly, for example, for young patients.

Usually, during total or partial replacement of shoulder, worn out humerus bone upper end head is replaced by a metallic sphere mounted on a support. Also a polyethylene or metallic coating can replace glenoid cavity of scapular bone.

The above support is usually comprised of a stem, introduced within the humerus diaphyseal portion. Said sphere, or metallic hemi-sphere, replacing the humerus head, is then fixed at the stem upper end by fixed joint or screw.

This kind of solution mainly has the following drawbacks:
  needing of complete removal of humerus epiphysial bone fragments, not completely replaced by metallic sphere or hemi-sphere. This problem does not permit any bone tissue recovery;
  often the phenomenon occurs by which stem element, inserted along the humerus axis, without acrylic cement, slides with respect to the same humerus toward the distal part of the channel.

Particularly the last phenomenon occurs since stem element is fixed to the humerus only by the inner walls of the diaphyseal channel digged by the surgery. Therefore, for example for osteoporosis tissues, anchoring is often not sure, thus requiring the use of acrylic cement.

Techniques exist providing modular prosthesis, such as that described in U.S. Pat. No. 6,783,549, permitting a reduced invasivity with respect to the standard prosthesis. More specifically, said patent provides prosthesis comprised of two elements. First element is applied to the humerus epiphysis by suitable fixing means, mainly mechanical means. Said application is carried out by a partial removal of epiphysial bone tissue. Finally, furthermore, second element is applied on said first element, suitable to reproduce the humerus head profile. Said second element can conform to the glenoid cavity.

Notwithstanding permitting a better compatibility and a bone tissue recovery higher, this kind of prosthesis in any case requires removal of the bone tissue. Furthermore, it cannot be used universally. Thus, its dimensions and proportions must be often adapted case by case.

A further problem of the above solutions is that they generally do not permit recomposition of the elements in case of multiple fractures.

In fact, main technical problems of the prosthesis presently used, as a direct consequence of the above, is the fact that it does not permits:
  perfectly oriented reconstruction of large and small tuberosity on the basis of anatomy;
  vascularization of still existing bone tissue and its restoring.

Therefore, in presence of young tissue and of a multiple fracture, bone tissue is not completely recovered, but rather removed to apply prosthesis.

Relevance of such a drawback is further underlined by the fact that it has been statistically revealed that shoulder dislocation and fractures, and particularly those concerning humerus, can be generically reduced at three or four fragments fractures. A first diaphyseal fragment, while others are epiphysial fragments. Particularly, epiphysial fragments generically provide two fragments at the base of the humerus head, in correspondence of the surgical neck, and a further fragment represented by the humerus head, suitable to insert within the glenoid cavity.

Therefore, in many cases it would be possible making recomposition of the head recovering bone tissue.

It is well evident that the above prosthesis and techniques are not satisfactory when applied in cases in which bone tissue could be recovered.

Object of the present invention is therefore that of suggesting a prosthesis modular and osteosynthesis prosthesis system suitable to be used in most cases of humerus epiphysial fractures, permitting the most recovery of bone tissue.

A second object of the present invention is that of permitting reconstruction of large and small tuberosity and preserving humeral head by original cartilage.

A third object of the present invention is that of permitting application of the above mentioned system in most number of cases of humerus proximal bone reconstruction and of the glena complementary part.

It is therefore specific object of the present invention an improved osteosynthesis modular prosthesis, particularly for humerus osteosynthesis, characterised in that it comprises a cup element having a convex surface suitable to be introduced within a bone cavity, particularly within the humerus glenoid cavity, and having a concave surface suitable to contain and keep joined all the bone fragments, particularly fragments of humerus epiphysial part, permitting vascularization and the consequent recovery of bone tissue, a stem element suitable to be introduced within a diaphyseal channel, particularly within humerus diaphyseal channel, a coupling element, and coupling means suitable to fix ends of said coupling element respectively at said cup element and at said stem element.

Always according to the invention, said coupling element can provide a curvature corresponding to the surgical neck profile.

Advantageously, according to the invention, said coupling means can fix said coupling element with the base of said cup element or with the concave surface of said coupling element.

Still according to the invention, said coupling means can be comprised of a cavity, and of an element suitable to engage with said cavity, said element preferably having a frusto-conical shape.

Furthermore, according to the invention, said cavity can be comprised of a shape memory material and/or by titanium alloy and/or titanium.

Advantageously, according to the invention, said stem element can have a cylindrical shape.

Preferably, according to the invention, said stem element can have a conical shape.

Still according to the invention, said prosthesis can comprise containment means that can be comprised of a screw suitable to couple with the concave surface of said cup element, said cup element comprising a threading on its concave surface.

Furthermore, according to the invention, said containment means can comprise a band suitable to tighten said epiphysial end, particularly humerus head.

Always according to the invention, said band can be comprised of memory shape material and can provide a through hole, though which said screw can be passed.

Still according to the invention, said containment means can comprise a wire having a first end fixed to the concave surface of said cup element and a second end fixed to a needle, so that said needle can be passed through the bone tissue and fixed to the humerus, maintaining bone fragments joined, particularly humerus epiphysial part fragments, cutting said wire and blocking the same by blocking means in the desired position.

Preferably, according to the invention, said wire can be a metallic wire.

Furthermore, according to the invention, said containment means can comprise at least a wire, suitable to be introduced within the bone tissue, and blocking means, suitable to block said at least a wire in the desired position.

Advantageously, according to the invention, said at least a wire can have a threading on at least an end.

Still according to the invention, said blocking means can comprise jaws, preferably comprised of metal and/or at least a plate and at least a screw.

Always according to the invention, said prosthesis can comprise anti-sliding means, provided on the lateral surface of said stem element, said anti-sliding means being suitable to create friction with the inner surface of said humerus diaphyseal channel.

Still according to the invention, said anti-sliding means can comprise a paste and/or a further band, preferably comprised of memory shape material.

Advantageously, according to the invention, said anti-sliding means can comprise acrylic cement.

Always according to the invention, said stem element can be comprised of an inner element and of an outer element, said outer element being suitable to be fixed within said diaphyseal channel, particularly humerus diaphyseal channel.

Furthermore, according to the invention, said outer element can have a cylindrical shape.

Still according to the invention, said stem element can comprise fixing means for fixing said inner element and said outer element, and said fixing means can comprise a threading on said inner element coupling with a corresponding threading on the inner surface of said outer element, so that when said inner element is threaded within said outer element, introduction depth can be adjusted.

Preferably, according to the invention, said fixing means can comprise a fixing material, such as acrylic cement.

Always according to the invention, said prosthesis can comprise a support element, suitable to be introduced at the base of the bone damaged epiphysial end, particularly at the humerus head base, said support element being integral with said coupling element or is an integral part of the same, and it can be coupled with said cup element.

Furthermore, according to the invention, said support element can have a polyhedral shape, e.g. a parallelepipedal or triangular pyramid shape Advantageously, according to the invention, said support element can be comprised of a plurality of rods, arranged as the corners of a polyhedron.

Still according to the invention, said support element can provide openings for realising guides for containment means and/or fixing means.

Always according to the invention, said cup element can be applied within said bone cavity.

It is further object of the present invention an osteosynthesis support element, particularly for humerus osteosynthesis, suitable to be used as prosthesis, said prosthesis comprising fixing means and like, characterised in that it is comprised of a plurality of rods, arranged as the corners of a polyhedron, so as to permit possible passage through its volume of fixing means for said prosthesis.

It is further object of the present invention a stem element suitable to be used as prosthesis, characterised in that it is comprised of an inner element and of an outer element, said outer element being suitable to be fixed within said diaphyseal channel, particularly humerus diaphyseal channel.

The present invention will be now described, for illustrative but not limitative purposes, according to its preferred embodiments, with particular reference to the figures of the enclosed drawings, wherein.

Figure 1:
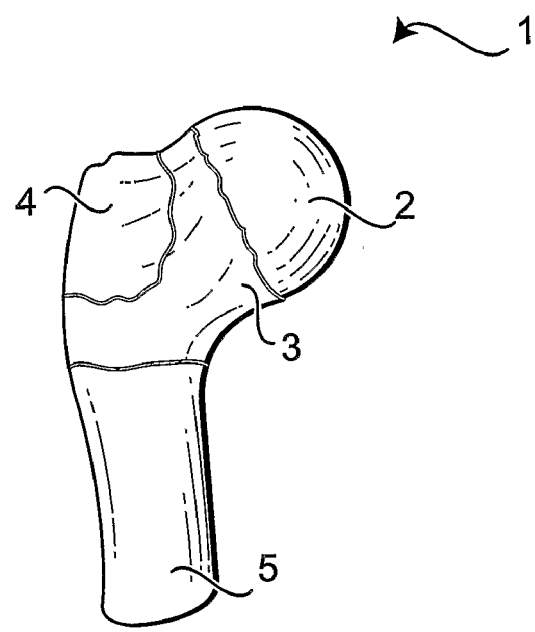
FIG. 1 shows typical humerus epiphysial fractures.

Making reference to FIG. 1, it is possible observing the parts where statistically it has been noted that humerus 1 fractures. Analysing the figure it is evident that often, obviously if bone tissue, age and other specific features permit it, it is possible recomposing fracture, thus parts of the head 2, of surgical neck 3 and 4 and diaphysial 5.

It clearly indicates that it would be suitable having at disposal a prosthesis permitting a fast application, a low invasivity level, and that can promote a progressive vascularization of bone tissue with its consequent recovery.

Figure 2:
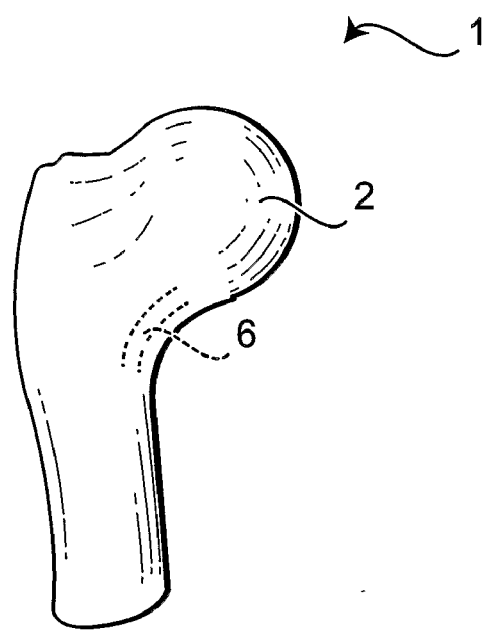
FIG. 2 shows a schematic section of humerus wherein a typical anatomical curvature.

Making now reference to FIG. 2, always on the basis of statistic studies, it has been revealed that human anatomy provides that curvature 6 in the surgical neck, under the head 2, is substantially constant independently from the age of the person.

On the basis of the above observation, it is possible realising a prosthesis that can be substantially adapted to all fractures and that can be comprised of a lower number of modular elements, as well as permitting an anatomical reconstruction promoting reconstruction of individual anatomic orientation of the humerus head.

Figure 3:
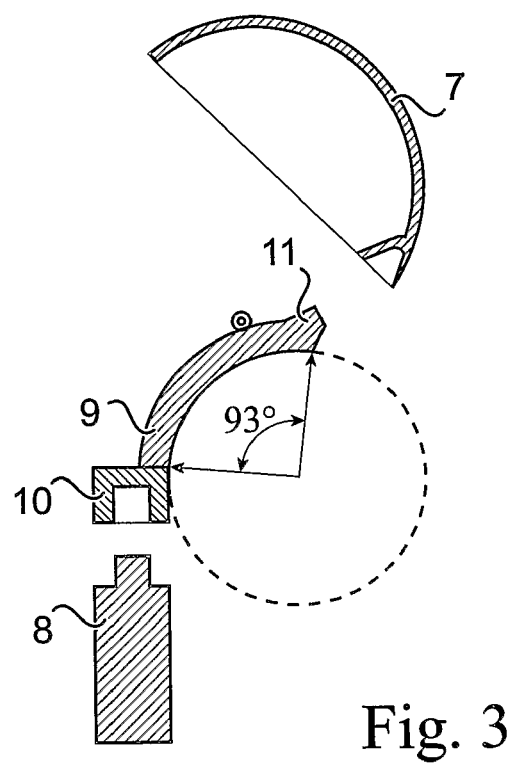
FIG. 3 shows an exploded section view of humerus modular prosthesis according to the present invention.

Making reference to FIG. 3, it is possible observing that above prosthesis is mainly comprised of three elements: a cup 7, a stem element 8 and a bridge or coupling element 9. The latter is suitable to couple by its ends with said cup 7 and said shaft 8.

Nowadays, in fact, among prosthesis instruments destined to the humerus head it is not provided a surface prosthesis component for humerus head fractures and a very small prosthesis permitting a complete medial reconstruction of the fracture.

Cup 7 has a concave shape. It has such a curvature to permit introduction of convex surface within glenoid cavity. Obviously, its measure and dimension will be a function of the patient anatomy.

Concave surface is suitable to receive and contain fracture bone fragments, permitting at the same time to keep them joined after the fracture recomposition.

Stem element 8 that is introduced by surgery within the humerus diaphysial channel can have a cylindrical or conical shape, according to the fixing needing, and that can have openings for fixing the same without cement (by screws).

Said bridge 9 is provided with coupling means 10, 11, suitable to permit fixing to the stem element 8 and to the cup 7, respectively, as it will be described in greater detail in the following.

Figure 4:
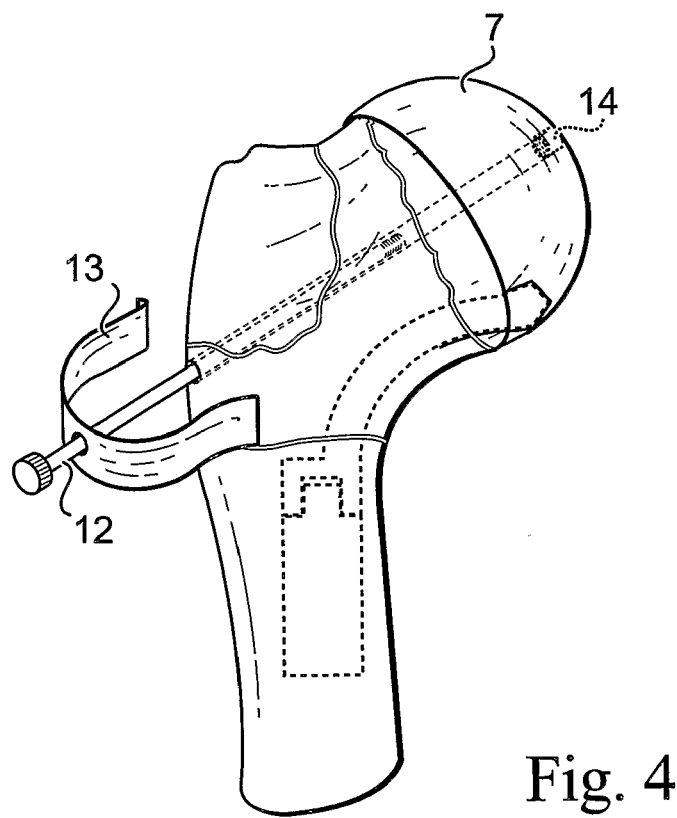
FIG. 4 shows a prosthesis according to FIG. 3 placed on a humerus.

FIG. 4 shows application of prosthesis according to the present invention to a humerus head 2 with a multiple fracture.

Stem element 8 is introduced within the humerus diaphyseal channel 5. Bridge 9 is coupled with said stem element 8 and said cup 7 by said means 10, 11. as already said, bridge 9 curvature is an anatomical constant, so that it is necessary providing a limited number of bridge element to adapt prosthesis to every anatomy.

Cup is maintained in its position by bridge 9, thanks to its concave surface. This permits containing fragments of fracture permitting vascularization of bone tissue and its restoring.

FIG. 4 also shows two further containment elements, particularly a screw 12 and a band 13.

Said screw 12 can be introduced in the rear part of the humerus head 2, coupling with a threading 14 realised on the concave surface of said cup 7.

Band 13 is comprised of a shape memory alloy. It promotes coupling of the fracture fragment. It is directly applied on the bone and is fixed on the screw 12 head.

It is possible providing a projection on the concave surface of the cup 7, in spite of screw 12 and band 13, and a flexible wire fixed to said projection (not shown in the figures). Said projection can be made integral with the diaphysial cortical, by tightening the wire passed through a suitable hole and fixed to the humerus. Once said wire is passed through bone tissue, connecting and fixing its parts, in order to recomposing the fracture. Wire is then cut, disposing the needle. Free end of the wire is then fixed to the humerus by standard fixing means, such as plates and like.

Figures 5, 5A:
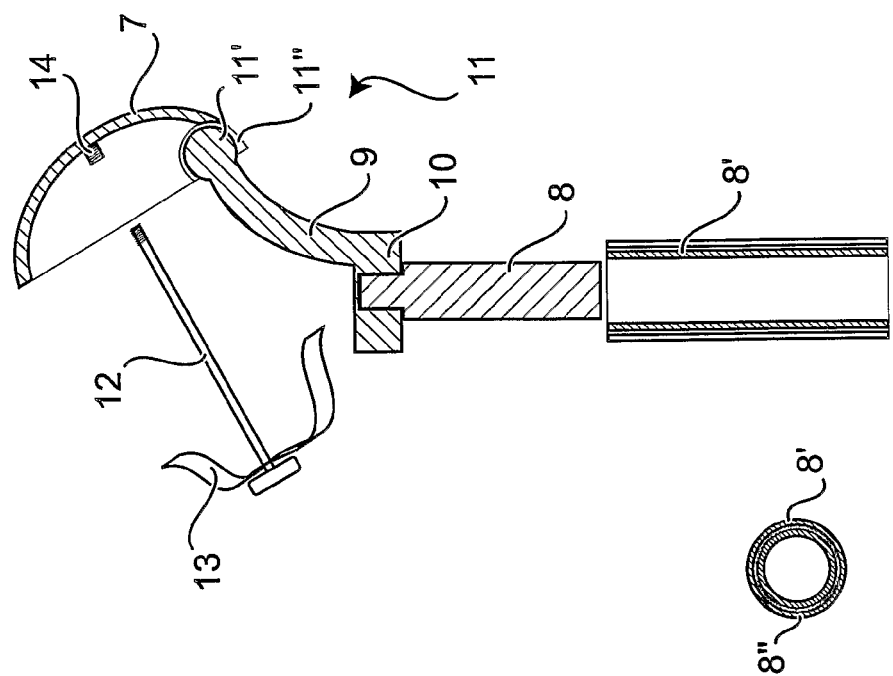
FIG. 5 shows a second embodiment of the prosthesis according to the present invention.
FIG. 5a shows a section view of the shaft on which a spiral band is applied for fixing stem element to the humerus bone tissue.

FIG. 5 shows a second embodiment of the present invention.

In this case, shaft 8 comprises a hollow cylinder 8' suitable to be introduced within the humerus diaphysial channel. This permits a higher mounting simplicity and replacing of the same prosthesis.

Fixing of shaft 8 within cylinder 8' can occur by screwing. This permits adjusting depth of introduction.

Furthermore, it is provided possibility of applying a paste or a second band 8'' on the cylinder 8' outer surface, as it can be observed from FIG. 5a. It permits more safely fixing cylinder 8', mainly in cases delicate or osteoporosis bones are involved.

Coupling means 11 are preferably comprised of a housing 11', obtained on the cup 7 edge, and an element 11', connected, at one end of the bridge 9 and suitable to engage with said housing 11'. Said housing 11' is comprised of shape memory material, so as to fix with element 11''. Said housing 11' can be also comprised of titanium alloy, or any other material.

Figure 7:
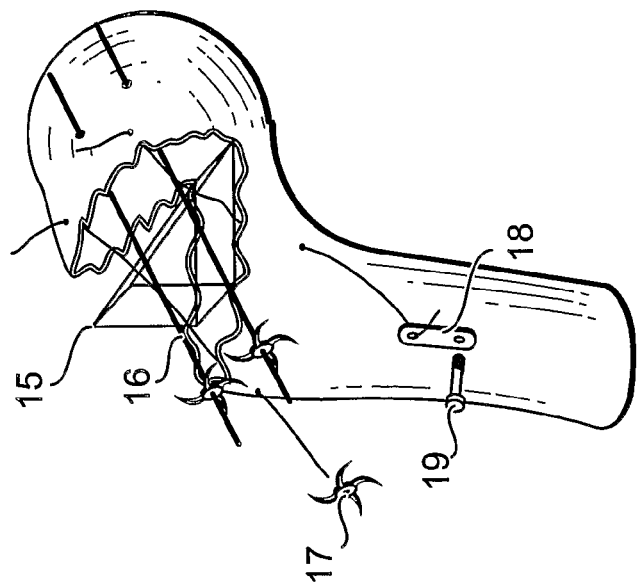
FIG. 7 shows a second embodiment of the prosthesis according to the present invention.
Figures 6, 6A:
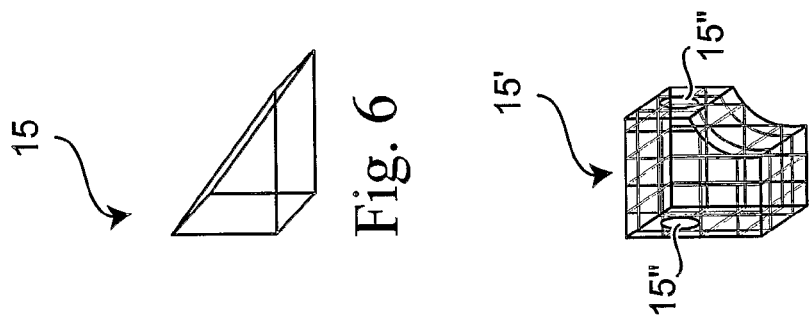
FIG. 6 shows a first embodiment of a prism shaped support element.
FIG. 6a shows a second embodiment of the support element.

A further embodiment of the present invention is shown in FIGS. 6, 6a and 7.

More specifically, FIGS. 6 and 6a show support structures 15 and 15', that in the embodiment of FIG. 6 has the shape of a parallelepiped with triangular base, to be inserted under the humerus head 2.

Said support structure 15 is comprised by an alloy network structure, wherein it is possible providing only elements along the main corners. Therefore, said prism 14 is hollow.

Said support structure 15 permits replacing fragments at the base of the head 2, when they cannot be recovered, when bone fragments are much damaged or squashed, and in any case supporting humerus head. The above support structure 15 is thus used as additional support. In other words, said support structure 15 is placed under the cup 7, if necessary.

Its network structure permits employing both the bridge 9 and the screws 12 and the band 13. particularly, screw 12 can even completely cross it, permitting its screwing with threading 14.

Said osteosynthesis support structure can be advantageously used alone for particular fractures of humerus osteosynthesis.

Support structure 15' of FIG. 6a has a more complex shape, to be possibly used for more serious fractures. In this case, it is provided a network and windows 15'' aligned each other, in order to permit guided passage of containment screws.

Said structures 15 or 15' permit replacing fragments at the base of the head 2, when they cannot be recovered, with bone fragments much damaged or squashed, and in any case supporting the humerus head. Above-mentioned structures 15 or 15' are used as additional support. In other words, said structures 15 or 15' are placed under the cup 7, if necessary. Network structure permits using both the bridge 9 and screws 12 and band 13. particularly, screw 12 can also completely cross it, in case support structure 15, permitting its screwing with threading 14.

After having reconstructed anatomy of humerus proximal tertius, placing in situ the support structure 15, preferably a triangular support structure, permitting supporting both large and small tuberosity, and after having positioned humerus head, from which cartilage has been removed, it is possible implanting, using said support structure 15, possibly integral or integrating the coupling element 9. Said support structure 15 thus permits reconstructing both bone proximal tertius and making a prosthesis of the partly destroyed cephalic prosthesis, with a prosthesis with a very small surface. In other words, support element 15, preferably comprised of titanium, represents a small stem occupying only meta-diaphysis on which cup element 7 can be implanted. Said cup element 7 can have central or coupling means 10-11, or they can be offset of few millimeters, such as a frusto-conical implant of about 3-4 cm, suitable to be fixedly coupled with a corresponding cavity realised on support elements 15 with a different dimension suitable to receive the same. In this way it is possible implanting a surface prosthesis on a fracture by the original technique of reconstruction.

It is possible using the above cup provided with projection and tension wire. Said wire can be passed through the network.

Said structure 15 or 15' can be crossed by and fixed to said cylindrical stem 8 with its distal and proximal portions holed so as to be used as a nail blocked for treating plural-fragments fractures of humerus head 2.

Thus use of a network structure is preferred since it permits:
  reducing weight of the same support structure and thus of the whole prosthesis;
  permitting the passage through its volume of further fixing elements.

FIG. 7 shows the use of parallelepiped 15. in case it is not necessary replacing head 2 by cup 7, it is in any case placing said parallelepiped 15, using it as the sole prosthesis element, always at the base of the humerus head, as support of the same bone and not of the prosthesis cup 7. Then, threaded or not wires of fiches 16 are applied, passing through the humerus head 2. they are fixed by anchoring means such as jaws 17, or jaws and plates 18, fixed by screws 19.

Obviously, said wires or fiches 16 can pass through the parallelepiped 15.

A further embodiment of the present invention provides that support element 15 is integral with bridge 9, or is an integral part of the same. In this case, support element 15 is not a network.

Said support element 15 can also be coupled with the cup 7 by a frusto-conical projection realised on the concave surface of the same, with a matching cavity.

On the basis of the previous specification, it can be noted that basic feature of the present invention is that it permits recovering damaged bone tissue, also due to disassembled fractures, promoting vascularization.

A first advantage of the present invention is the fact that it permits faster recovery time.

A second advantage of the present invention is that prosthesis, having the minimum dimension, permits an optimum view of where fixing on the rear part the rotator cuff, and proper orientation of cartilaginous surface.

Furthermore, providing a reduced number of elements permits a quick choice and assembling of prosthesis elements better conforming to the patient anatomy, with a high adaptability to different patients.

A third advantage of the present invention is that of permitting reconstruction of large and small tuberosity.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. Improved humeral osteosynthesis modular prosthesis, comprising:
  a stem element (8) insertable within a humerus diaphyseal channel;
  a cup element (7) having a convex surface suitable to be introduced within a humerus glenoid cavity;
  a coupling element (9) having a first and a second end and comprising first coupling means (11), suitable to couple said first end to said cup element (7) and second coupling means (10) suitable to couple said first end to said stem element (8); characterised in that said cup element (7) has a concave surface suitable to contain and keep joined all the bone fragments of humerus epiphysial part, permitting vascularization and the consequent recovery of bone tissue; and said coupling element (9) has a curvature (6) corresponding to the surgical neck profile of said bone, said curvature (6) being an anatomical constant of the surgical neck of the human humerus, said coupling element comprising a cavity (11") provided on a lower edge of said cup element (7) and of a shape memory material or titanium alloy or titanium, and an element (11') connected at one end of the coupling element (9) and configured to engage said cavity (11") so that said coupling element (9) is coupled to a portion of the lower edge of said cup element (7), said element (11') having a frusto-conical shape.

2. Prosthesis according to claim 1, characterised in that said coupling means (10, 11) fix said coupling element (9) with the base of said cup element (7).

3. Prosthesis according to claim 1, characterised in that said first coupling means (11) couple said coupling element (9) with the concave surface of said cup element (7).

4. Prosthesis according to claim 1, characterised in that said stem element (8) has a cylindrical shape.

5. Prosthesis according to claim 1, characterised in that said stem element (8) has a conical shape.

6. Prosthesis according to claim 1, characterised in that said prosthesis comprises containment means (12, 13).

7. Prosthesis according to claim 6, characterised in that said containment means are comprised of a screw (12) suitable to couple with the concave surface of said cup element (7), said cup element (7) comprising a threading (14) on its concave surface.

8. Prosthesis according to claim 6, characterised in that said containment means comprise a band (13) suitable to tighten said epiphysial end, particularly humerus head.

9. Prosthesis according to claim 8, characterised in that said band (13) is comprised of memory shape material.

10. Prosthesis according to claim 8, characterised in that said band (13) provides a through hole, though which said screw (12) is passed.

11. Prosthesis according to claim 6, characterised in that said containment means comprise a wire having a first end fixed to the concave surface of said cup element (7) and a second end fixed to a needle, so that said needle can be passed through the bone tissue and fixed to the humerus, maintaining humerus epiphysial part fragments joined, cutting said wire and blocking the same by blocking means in the desired position.

12. Prosthesis according to claim 11, characterised in that said wire is a metallic wire.

13. Prosthesis according to claim 6, characterised in that said containment means comprise at least a wire, suitable to be introduced within the bone tissue, and blocking means, suitable to block said at least a wire in the desired position.

14. Prosthesis according to claim 13, characterised in that said at least a wire has a threading on at least an end.

15. Prosthesis according to claim 11, characterised in that said blocking means comprise griffes (17).

16. Prosthesis according to claim 11, characterised in that said blocking means comprise at least a plate (18) and at least a screw (19).

17. Prosthesis according to claim 1, characterised in that said prosthesis comprises anti-sliding means, provided on the lateral surface of said stem element, said anti-sliding means being suitable to create friction with the inner surface of said humerus diaphyseal channel.

18. Prosthesis according to claim 17, characterised in that said anti-sliding means comprise a paste or a further band.

19. Prosthesis according to claim 17, characterised in that said anti-sliding means comprise acrylic cement.

20. Prosthesis according to claim 1, characterised in that said stem element is comprised of an inner element (8) and of an outer element (8'), said outer element (8') being suitable to be fixed within said humerus diaphyseal channel.

21. Prosthesis according to claim 20, characterised in that said outer element (8') has a cylindrical shape.

22. Prosthesis according to claim 20, characterised in that said stem element (8) comprises fixing means for fixing said inner element and said outer element (8').

23. Prosthesis according to claim 22, characterised in that said fixing means comprise a threading on said inner element (8) coupling with a corresponding threading on the inner surface of said outer element (8'), so that when said inner element (8) is threaded within said outer element (8'), introduction depth can be adjusted.

24. Prosthesis according to claim 22, characterised in that said fixing means comprise a fixing material.

25. Prosthesis according to claim 1, characterised in that said prosthesis comprises a support element (15; 15') comprised of a plurality of rods forming a network structure, forming the corners of a hollow polyhedron, and it is insertable into the bone tissue so as to replace fragments of said bone tissue, to keep joined all the neighbouring bone fragments and to internally support said bone tissue, in order to aid the vascularization and the consequent recovery of said bone tissue inside and around itself.

26. Prosthesis according to claim 25, characterised in that said support element is integral with said coupling element (9) or is an integral part of the same, and can be coupled with said cup element (7).

27. Prosthesis according to claim 25, characterised in that said support element (15, 15') has a polyhedral shape.

28. Prosthesis according to claim 25, characterised in that said polyhedron is a parallelepipedal or triangularly shaped pyramid.

29. Prosthesis according to claim 25, characterised in that said support element is comprised of a plurality of rods, forming the corners of a polyhedron.

30. Prosthesis according to claim 25, characterised in that said support element provides openings (15") for realising guides for containment means or fixing means.

31. Prosthesis according to claim 1, characterised in that said cup element (7) is applied within said bone cavity.

32. Osteosynthesis support element (15; 15') for humerus osteosynthesis, characterised in that said support element (15; 15')
is comprised of a plurality of rods forming a network structure, forming the corners of a hollow polyhedron, and
in that it is insertable into the bone tissue so as to replace fragments of said bone tissue, to keep joined all the neighbouring bone fragments and to internally support said bone tissue, in order to aid the vascularization and the consequent recovery of said bone tissue inside and around itself.

33. Support element (15; 15') according to claim 32, characterised in that it is suitable both to be used as prosthesis and as a support element, maintained in place by fixing means passing through its internal volume.

34. Support element (15; 15') according to claim 32, characterised in that said polyhedron is a parallelepiped, or a triangular base pyramid.

35. Support element (15; 15') according to claim 32, characterised in that said rods are comprised of light alloy.

36. Support element (15; 15') according to claim 32, characterised in that it comprises openings (15") for realising guides for containment means and/or fixing means.

37. Stem element for osteosynthesis prosthesis characterised in that it is comprised of an inner element (8) and of an outer cylinder (8'), said outer cylinder (8') being suitable to be fixed within a diaphyseal channel.

38. Stem element according to claim 37, characterised in that it comprises fixing means for fixing said inner element and said outer cylinder.

39. Stem element according to claim 38, characterised in that said fixing elements comprise a threading on said inner element coupling with a corresponding threading on the inner surface of said outer cylinder (8'), so that when said inner element (8) is threaded within said outer cylinder (8'), introduction depth can be adjusted.

40. Stem element according to claim 38, characterised in that said fixing means comprise a fixing material.

* * * * *